United States Patent
Lukanidin et al.

(10) Patent No.: US 6,468,960 B1
(45) Date of Patent: Oct. 22, 2002

(54) THERAPEUTIC COMPOSITIONS AND METHODS FOR ENHANCING ANGIOGENESIS

(75) Inventors: Eugene M. Lukanidin; Noona Ambartsumian, both of Copenhagen (DK)

(73) Assignee: Prolifia, Inc., Tucson, AZ (US)

( * ) Notice: Subject to any disclaimer, the term of this patent is extended or adjusted under 35 U.S.C. 154(b) by 0 days.

(21) Appl. No.: 09/553,532

(22) Filed: Apr. 20, 2000

Related U.S. Application Data
(60) Provisional application No. 60/130,892, filed on Apr. 23, 1999.

(51) Int. Cl.$^7$ .................. A61K 38/00; A61K 38/16; A61K 38/17; C07K 2/00
(52) U.S. Cl. ................. 514/2; 530/300; 530/350; 530/351; 424/184.1; 424/198.1; 424/85.1
(58) Field of Search .................... 514/2, 530, 350, 514/12; 530/300, 350, 399, 351; 424/85.1, 184.1, 198.1, 93.21

(56) References Cited

U.S. PATENT DOCUMENTS
5,798,257 A  8/1998  Zain et al. ................ 435/252.3

OTHER PUBLICATIONS

Skolnick et al. From genes to protein structure and function: novel applications of computational approaches in the genomic era. Trends in Biotech 18(1): 34–39, 2000.*
Bork, A. Powers and pitfalls in sequence analysis: the 70% hurdle. Genome Res 10: 398–400, 2000.*
Doerks et al. Protein annotation: detective work for function prediction. Trends in Genetics 14(6):248–250, 1998.*
Smith et al. The challenges of genome sequence annotation or "The devil is in the details". Nature Biotech 15: 1222–1223, 1997.*
Brenner, S.E. Errors in genome function. Trends in Genetics 15(4): 132–133, 1999.*
Bork et al. Go hunting in sequence databases but watch out for the traps. Trends in Genetics. 12(10): 425–427, 1996.*
Wells. J.A. Additivity of mutational effects in proteins. Biochemistry 29 (37): 8509–8517, 1990.*
Ngo et al. Computational complexity, protein structure prediction, and the Levinthal paradox. The Protein Folding Problem and Tertiary Structure Prediction, pp. 492–495, 1994.*
Simons et al. Clinical trials in coronary angiogenesis: issues, problems, consensus. Circulation 102: 73–86, 2000.*
Pettit et al. The development of site–specific drug–delivery systems for protein and peptide biopharmaceuticals. Trends Biotechnol 16: 343–349, 1998.*

Lazarous DF, Shou M, et al. Pharmacodynamics of basic fibroblast growth factor: route of administration determines myocardial and systemic distribution. Cardiovascular Research 36 (1997) 78–85.*
Ford, H.L., et al. (1995) "Interaction of metastasis associated Mts1 protein with nonmuscle myosin", Oncogene10:1597–1605.
Gimbrone, M.A. Jr., et al. (1972) "Tumor Dormancy In Vivo by Prevention of Neovascularization", The Journal of Experimental Medicine136:261–276.
Klingelhöfer, J., et al. (1997) "Expression of the Metastasis–Associated mts1 Gene During Mouse Development", Development Dynamics210:87–95.
Kriajevska, M., et al. (1998) "Metastasis –associated Mts1 (S100A4) Protein Modulates Protein Kinase C Phosphorylation of the Heavy Chain of Nonmuscle Myosin", The Journal of Biologica Chemistry273 (16) :9852–9856.
Folkman, J., et al. (1989) "Induction of angiogenesis during the transition from hyperplasia to neoplasia", Nature339:58–61.
Kriajevska, M.V., et al. (1994) "Non–muscle Myosin Heavy Chain as a Possible Target for Protein Encoded by Metastasis–related mts–1 Gene", The Journal of Biological Chemistry269(31):19679–19682.
Schäfer, B.W., et al. (1996) "The S100 family of EF–hand calcium–binding proteins: functions and pathology", TIBS21:134–140.
Skobe, M., et al. (1997) "Halting angiogenesis suppresses carcinoma cell invasion", Nature Medicine3(11):1222–1227.
Takenaga, K., et al. (1994) "Involvement of S100–related Calcium–binding Protein pEL98 (or mts1) in Cell Motility and Tumor Cell Invasion", Jpn. J. Cancer Res.85:831–839.
Watanabe, Y., et al. (1993) "Calvasculin, as a factor affecting the microfilament assemblies in rat fibroblasts transfected by src gene", FEBS324(1):51–55.
Zimmer, D.B., et al. (1995) "The S100 Protein Family: History, Function, and Expression", Brain Research Bulletin37(4):417–429.

* cited by examiner

*Primary Examiner*—Elizabeth Kemmerer
(74) *Attorney, Agent, or Firm*—Scully, Scott, Murphy & Presser

(57) ABSTRACT

The present inventors have surprisingly found that the Mts-1 protein stimulates angiogenesis. In particular, the present inventors have found that Mts-1 transgenic mice developed hemangiomas and stenosis. The present inventors have also found that addition of Mts-1 proteins to the culture media increases the motility of mouse endothelial cells. Further, the present inventors have found that injection of Mts1 proteins stimulates angiogenesis in the mouse corneas. Accordingly, the present invention provides methods of enhancing angiogenesis in a subject in need thereof by administering a therapeutically effective amount of an angiogenic Mts-1 component.

9 Claims, 5 Drawing Sheets

(2 of 5 Drawing Sheet(s) Filed in Color)

THERAPEUTIC COMPOSITIONS AND METHODS FOR ENHANCING ANGIOGENESIS

CROSS REFERENCE TO RELATED APPLICATIONS

This application claims priority from U.S. Provisional Application No. 60/130,892, filed on Apr. 23, 1999.

FIELD OF THE INVENTION

This invention relates to compositions and methods for enhancing angiogenesis. More particularly, the invention relates to the use of the Mts-1 gene or Mts-1 protein for enhancing angiogenesis in human and animal subjects.

BACKGROUND OF THE INVENTION

Angiogenesis is a process by which new blood vessels are generated into a tissue or organ. Angiogenesis in rarely observed in normal tissues in humans and animals. Angiogenic factors from pathological tissues of various kinds have been characterized and isolated, such as those from solid tumors (Folkman et al. *J. Exp. Med.* 133: 275, 1971), from synovial fluid (Brown et al., *Lancet* I: 682:685, 1980), from human mayocardial infarcts (Kumar et al., *Lancet* II: 364–367, 1983), from the vitreous fluid of humans with diabetic retinopathy and in the retinas of animals (Hill et al., *Experientia* 39: 583–585, 1983; D. Amore et al., *Proc. Natl. Acad. Sci. USA* 78: 3068–3073, 1981; Kissun et al., *Br. J. Ophth.* 66: 165–169, 1982), and from wound fluid (Branda et al., *Proc. Natl. Acad.Sci. USA* 79: 7773–7777, 1982).

Endothelial cells and pericytes, surrounded by a basement membrane, form capillary blood vessels. Angiogenesis begins with the erosion of the basement membrane by enzymes released from endothelial cells and leukocytes. The endothelial cells, which line the lumen of blood vessels, then protrude through the basement membrane. Angiogenic stimulants induce the endothelial cells to migrate through the eroded basement membrane. The migrating cells formula "sprout" off the parent blood vessel, where the endothelial cells undergo mitosis and proliferate. Eventually, the endothelial sprouts merge with each other to form capillary loops, creating the new blood vessel.

For a general review of angiogenisis, see Maciag, T., *Molecular and Cellular Mechanisms of Angiogenesis*, in IMPORTANT ADV. ONCOL., pp. 85–98, 1990.

Mouse, rat and human Mts-1 genes have been previously identified and isolated (Linzer et al., *Proc. Natl. Acad.Sci. USA* 80: 4271–4275, 1983, Barraclogh et al., J. Mol. Biol. 198: 13–20, 1987 and U.S. Pat. No. 5,798,257 to Zain et al.). The Mts-1 protein, as a calcium binding protein, is believed to have a role in cell growth and myoepithelial cell differentiation. U.S. Pat. No. 5,798,257 discloses that the mammalian Mts-1 gene is expressed at 10–100 fold higher levels in metastatic cells compared to non-metastatic cells and normal cells, and thus, that an increased expression of the Mts-1 gene within a cell or tissue is diagnostic of metastatic cancer. The role of Mts-1 in angiogenesis has not been reported prior to the present invention.

SUMMARY OF THE INVENTION

The present inventors have uniquely identified that the Mts-1 protein stimulates angiogenesis. Accordingly, the present invention is directed to the use of angiogenic Mts-1 components in therapeutic compositions and methods for enhancing angiogenesis in a subject in need thereof.

The therapeutic compositions and methods of the present invention are useful for any situations in which angiogenesis is inadequate and is clinically required, such as damaged tissues or organs, or transplanted tissues or organs. The compositions and methods of the present invention are particularly useful for patients suffering a cardiac condition (e.g., patients after bypass surgery or heart transplant), patients suffering tissue damage in the skin, gastrointestinal tract, urinal tract, as well as a vascular tissues resistant to vascularization such as the knee, the wrist or the joint, patients who have suffered a stroke and any other patients in need of angiogenesis.

An angiogenic composition of the present invention can include an Mts-1 component, e.g., an Mts-1 protein, a functional fragment or analog of an Mts-1 protein, as well as nucleic acid molecules encoding such proteins, fragments or analogs.

Angiogenic compositions of the present invention can suitably include other substances that are appropriate or desirable for angiogenesis. These substances can include any other angiogenic compounds, growth hormones, growth factors, biologically active segments of growth factors, interleukins, polysaccharides, or mixtures thereof.

Angiogenic Mts-1 components suitable for use in the present methods are preferably provided in a pharmaceutically acceptable carrier, such as oils, water, saline solutions, gel, lipids, liposomes, resins, porous matrices, binders, fillers and the like, or combinations thereof.

The angiogenic compositions can be administered to a subject in need of angiogenesis by standard routes, including the oral, ophthalmic, nasal, topical, transdermal, parenteral, intracranial, intracerebral, intraspinal, intravaginal, intrauterine, or rectal route, or by injection or surgical implantation proximate to a preselected tissue or organ site.

DESCRIPTION OF DRAWINGS

The file of this patent contains at least one drawing executed in color. Copies of this patent with color drawing(s) will be provided by the Patent and Trademark Office upon request and payment of the necessary fee.

A.—stenosis, HE-staining, magnification x400;

B.—hemangioma, HE-staining magnification x40;

C.—immunofluorescent staining of stenotic lesion with anti-smooth muscle actin antibodies, magnification x400;

D.—immunohistochemical staining of stenotic lesion, x400;

E.—immunohistochemical staining of hemangioma with anti-S100A4(mts1) antibodies, x400.

Figure 1A:
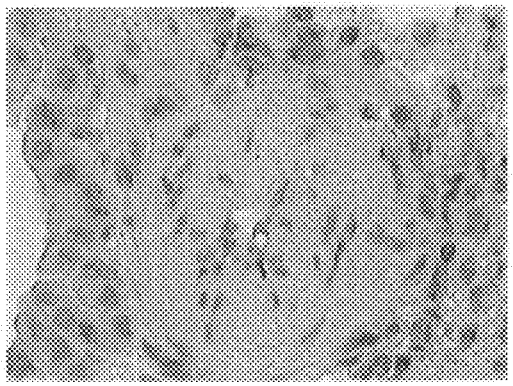
FIG. 1 depicts pathologies observed with the HMGCR/mts1 transgenic mice.
Figure 1B:
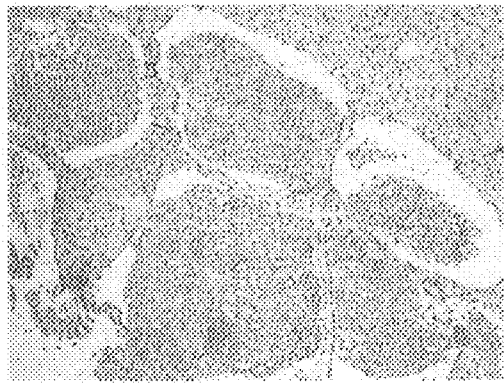
Figure 1C:
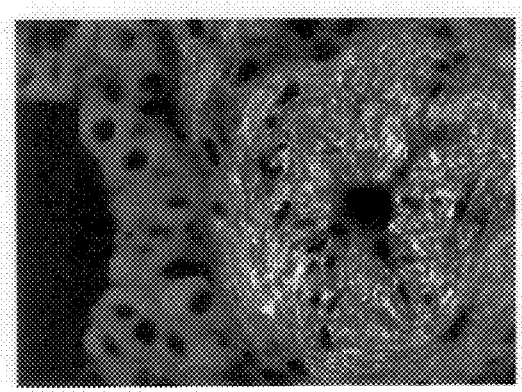
Figure 1D:
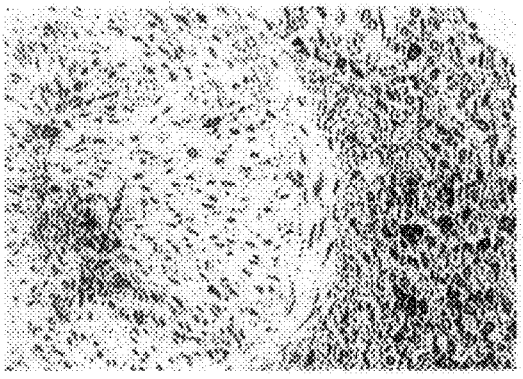
Figure 1E:
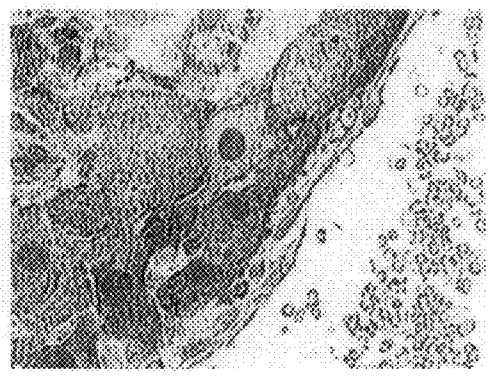
Figure 2A:
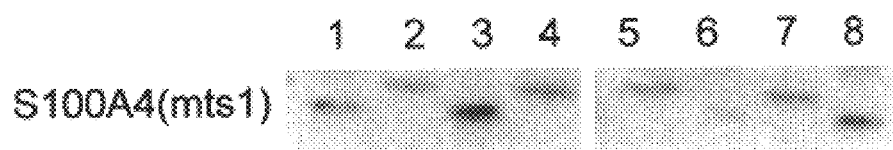
Figure 2B:
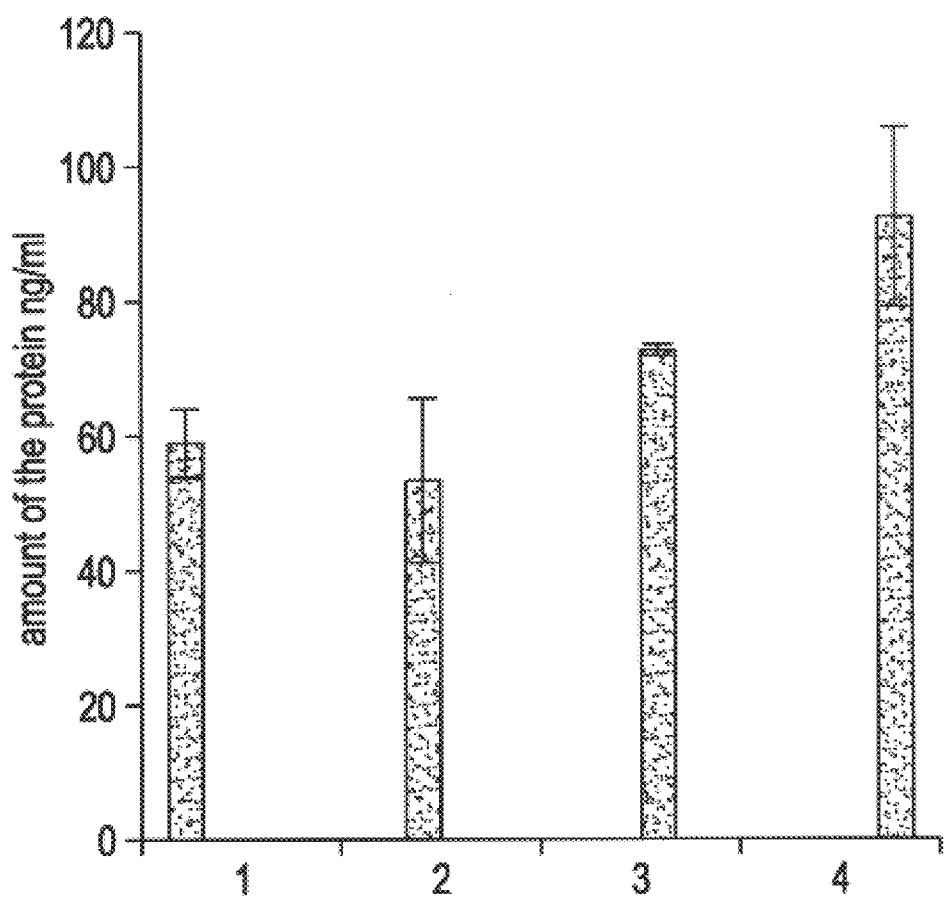
Figure 3A:
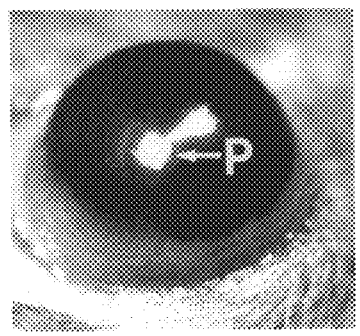
Figure 3B:
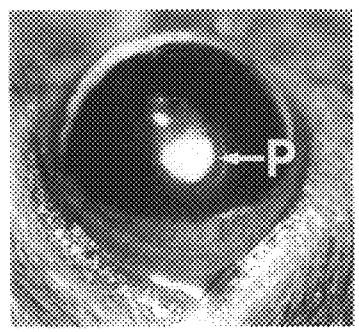
Figure 3C:
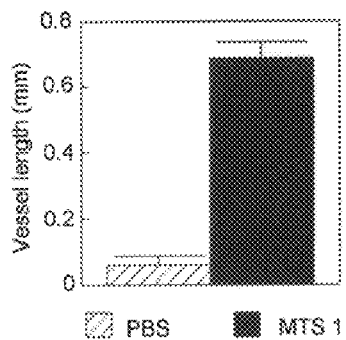
Figure 3D:
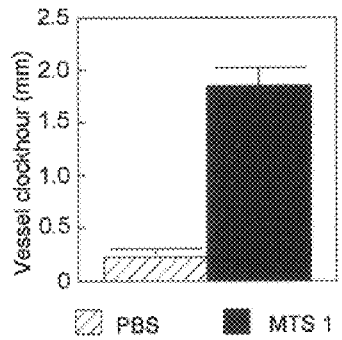
Figure 3E:
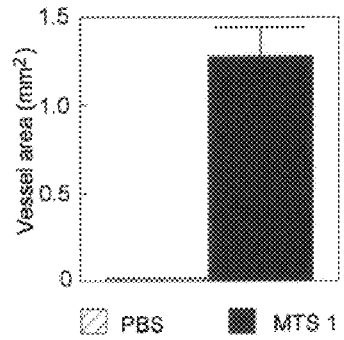

FIG. 2 depicts the detection of the S100A4(mts1) in the blood of the HMGCR/mts1 transgenic animals.

A. Immunoprecipitation of the S100A4(mts1) from the blood serum of individual transgenic (lanes 1,3) and non-transgenic (lanes 6,8) animals. Lanes 2,4,5 and 7 represent corresponding negative controls. Detection was achieved by Western-blot analysis.

B. Quantitation of the amount of the S100A4(mts1) protein (ng/ml) by sandwich ELISA.

1. nontransgenic animals 02–16 months (n=17);

2. nontransgenilc animals 17–26 months (n=5);

3. transgenic animals 02–16 months (n=5);

4. transgenic animals 17–26 months (n=10).

Each measurement for individual animals was performed 3 times. Bars represent means of these measurements ±SD.

FIG. 3 depicts the stimulation of corneal neovascularization by S1000A4(mts1). Pellets of sucrose aluminum sulfate and hydron polymer containing 320 ng of S100A4(mts1) (B) and PBS alone (A) were implanted into corneal micropockets of C57B16/J mice as described in Example 2. Corneas were photographed by a slit-lamp stereomicroscope on day 5 after growth factor implantation. Photographs represent 20×amplification of the mouse eye. P=Pellets. Arrows point to the implanted pellets. Corneal neovascularization was quantitated as to maximal vessel length (C), clock hours of circumferential neovascularization (D) and area of neovascularization (E). Graphs represent mean values (±S.D.) of 10 eyes (5 mice) in each group.

FIG. 4 depicts the effect of the recombinant S100A4 (mts1) on motility of mouse endothelial SVEC4–10 cells in vitro. Cells were grown on Matrigel for 24 h. One hour before analysis culture medium was changed and the recombinant S100A4(mts1) was added.

a. Effect of various concentrations of the protein on mean-cell-speed of the cells. The mean-cell speed is expressed as a percent of control. Each data point represents the mean of 3–8 individual experiments. In each experiment motility of 75–120 individual cells was measured. Bars denote mean±SD.

b. Effect of 0.15 $\mu$M S100A4(mts1) on mean-square-displacement of SVEC4–10 cells. Data for one representative experiment are shown. 10 different microscopic fields were recorded. The number of cells in the individual experiments were 75(control) and 89–0.5 $\mu$M S100A4 (mts1). Data points are expressed as ($d^2$). Lines indicate curve fitting to the equation $(d^2)=2S^2P(\tau-P(1-e^{\tau/P}))$ c. Effect of the anti-S100A4(mts1) antibodies (1:200) on motility of SVEC4–10 cells treated with S100A4(mts1) (0.5 $\mu$M) and the Y75F mutant of S100A4 (mts1). Each data point is the mean of 4 individual experiments. In each experiment motility of 80–115 individual cells was analyzed. Bars denote mean±SD. (P value<0.01)

Figure 5A:
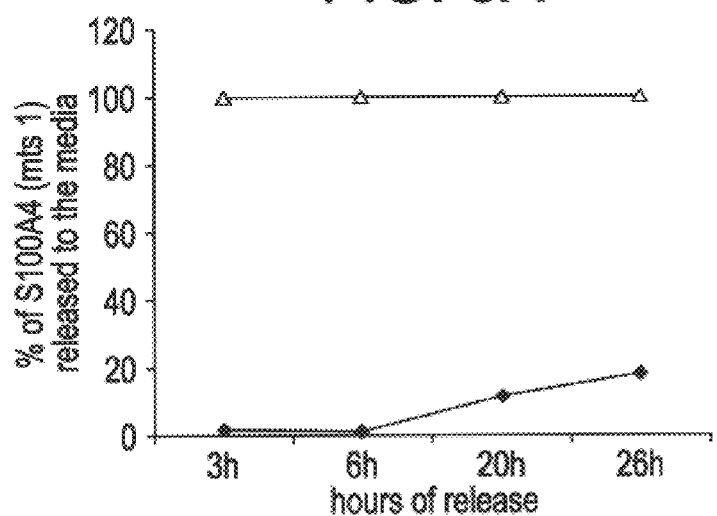
Figure 5B:
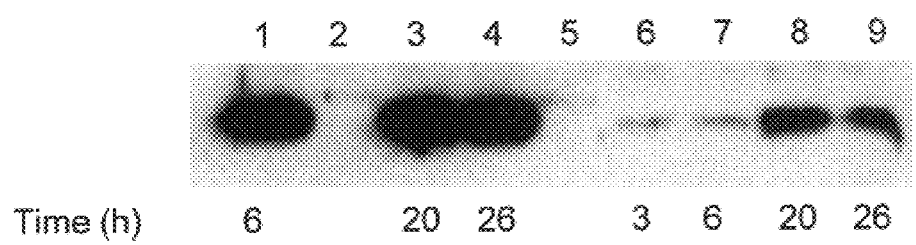
Figure 5C:
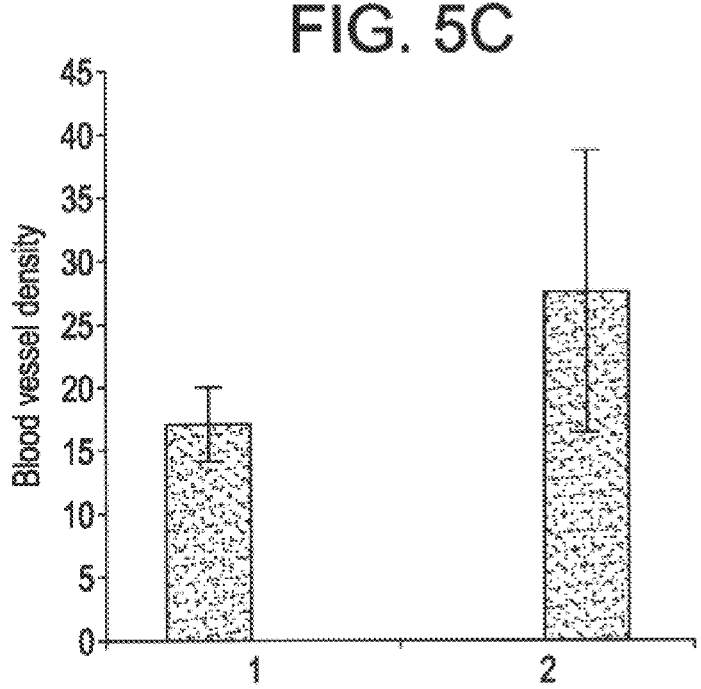

FIG. 5 depicts the release of the S100A4(mts1) from the tumor cell lines and determination of the blood vessel density in the S100A4(mts1) expressing tumors. Immunoprecipitation of S100A4 (mts1) from supernatants of VMR-Liv and CSML100 cell lines.

A. Kinetics of release of $^{35}$S labelled S100A4(mts1) protein from VMRLiv cells. The cells were induced to express S100A4(mts1) protein for 24 h prior to the labelling. Viability of the cells was tested in LDH assay (-Δ-). The results of typical experiment are presented as a percent from the total amount of the S100A4(mts1) immunoprecipitated from the cells and supernatant(-♦-).

B. Western blot analysis of the S100A4(mts1) protein immunoprecipitated from the CSML100 cells. (1,3,4)—cell lyzates; (6–9)—supernatants. The filters were developed with polyclonal anti-S100A4(mts1) antibodies. 2,5-negative, controls for the cells and supernatant respectively.

C. Measurements of the blood vessel density of transgenic and nontransge nic tumors of GRS/Amts1 hybrid transgenic mice. Tumor sections were stained with CD31 (PECAM-1) antibodies and the vessel density was determined as described in Example 4. Bars represent mean vascular density ±SD counted for 10 tumors in each group (P value<0.024).

DETAILED DESCRIPTION OF THE INVENTION

The present inventors have surprisingly found that the Mts-1 protein stimulates angiogenesis. For example, the present inventors have found that Mts-1 transgenic mice developed hemangiomas and stenosis. Hemangioma, a benign tumor of vascular origin, is extremely rare among normal mice populations. Stenosis, characterized by a extreme development of smooth muscle cells surrounding the blood vessels, has not been described in mice prior to the present invention. The present inventors have also found that addition of Mts1 proteins to the culture media increases the motility of mouse endothelial cells. Further, the present inventors have found that injection of Mts1 proteins stimulates. angiogenesis in the mouse corneas.

Accordingly, the present invention provides therapeutic compositions and methods for enhancing angiogenesis in a subject in need thereof.

As used herein, the term "angiogenesis" refers to the process by which new blood vessels are formed into a tissue or organ with accompanying increased blood circulation. The process of angiogenesis involves migration and proliferation of endothelial cells, which line the lumen of blood vessels.

Angiogenesis is observed in humans and animals only in restricted situations, for example, in wound healing, fetal and embryo nal development and formation of the endometrium and placenta. Unregulated angiogenesis occurs in a number of pathological conditions, such as tumor metastasis.

By "enhancing angiogenesis" it means stimulating, accelerating or potentiating the process of blood vessel formation of large and small vessels, as well as capillaries. The terms "enhancing angiogenesis" and "increased vascularization" are used herein interchangeably.

The term "subject" is taken to mean any animal subject, preferably, a human subject. "A subject in need of enhanced angiogenesis" refers to a subject suffering a condition where vascularization is inadequate and angiogenesis is clinically required, for example, in the treatment of damaged tissues or organs, or in keeping the transplanted tissues or organs alive.

The present invention particularly contemplates subjects who suffer a cardiac disease, for example, a patient who has undergone transplantation of a heart or heart tissue or bypass surgery. For patients who are likely to suffer cardiac attacks, administration of an angiogenic composition including an Mts-1 component can prevent heart attacks by increasing the blood circulation through new blood vessels to the anginal cardiac tissue before the tissue becomes infarcted. For patients who have already suffered myocardiac infarction, the present methods of enhancing angiogenesis can speed recovery. Thus, the present methodology can be applied to patients before, during or after infarction.

The present indention also contemplates subjects suffering tissue damage due to surgery, burns, fracture, laceration, or infection. The tissues to which the present methods of enhancing angiogenesis are applicable include skin, gastrointestinal tract, urinal tract, as well as avascular tissues resistant to vascularization such as the meniscus of the knee or the wrist, or the end of the clavicle, or the temporomandibular joint. Angiogenic compositions including an Mts-1 component can be administered into the subject, or in cases of tissue or organ transplant, the angiogenic compositions can be incorporated into such tissues or organs before the transplant. The tissues and organs include those artificially designed, such as skin equivalents described in U.S. Pat. Nos. 4,418,691 and 5,273,900, and bioartificial organs described in U.S. Pat. Nos. 5,843,431 and 5,002,661.

Another type of subject contemplated by the present invention include those who have suffered stroke or an ischemic attack. Angiogenesis is desirable to enhance blood flow to the nervous system, such as the cerebral cortex and spinal cord.

Other subjects contemplated by the present invention include patients with vascular problems in peripheral vessels, e.g., diabetics with peripheral vascular pathologies, and patients with infertility due to inadequate vascularization of the uterine endometrium.

The therapeutic compositions and methods of the present invention are also useful in promoting vascularization of relatively avascular tumors for enhanced delivery of antitumor substances. In addition, the present methods can be effective in treating hardened capsules usually formed around foreign-body implants such as mammary implants, penile implants and artificial urinary sphincters.

In one embodiment, the present invention provides angiogenic compositions which include an Mts-1 component. A preferred Mts-1 component is an Mts-1 protein or a functional fragment thereof, preferably, a human Mts-1 protein or a functional fragment thereof. U.S. Pat. No. 5,801,142, which describes the sequence of human Mts-1 protein and how to make a human Mts-1 protein and fragments thereof, is incorporated herein by reference.

As used herein, the term "functional fragment" refers to a fragment of an Mts-1 protein, having a sufficient length to be angiogenic. According to the present invention, a functional fragment of an Mts-1 protein can be as short as 6 amino acid in length, preferably, as small as 8 or 9 amino acid in length, more preferably, as small as about 15 amino acid in length.

A variety of well-known bioassays can be employed to determine whether a peptide fragment of an Mts-1 protein is angiogenic. These assays include assays of the motility of cultured endothelial cells, mouse corneal assays, and immunohistological assays of the vascularization of implanted tumors in animals following the administration of a protein or peptide of interest. These assays are described in detail hereinafter. In addition, chick CAM assays and bovine capillary endothelial cell proliferation assays can be employed and are well known in the art (e.g., described by O'Reilly et al. *Cell* 79: 315–328, 1994). In a chick CAM assay, 3-day-old chicken embryos with intact yolks are separated from the egg and placed in a petri dish. After 3 days of incubation a methylcellulose disc containing the protein to be tested is applied to the CAM of individual embryos. After 48 hours of incubation, the embryos and CAMs are examined to determine whether endothelial growth has been enhanced.

Peptide analogs of functional fragments of a Mts-1 protein are also contemplated by the present invention. "Peptide analogs" refers to variants of an Mts-1 peptide having substitutions, insertions or deletions of one or more amino acid residues, or having modifications on the side groups of amino acid residues and which maintain the intended function.

Another preferred Mts-1 component is a nucleic acid molecule coding for an Mts-1 protein, preferably, a human Mts-1 protein, or functional fragments thereof.

Preferably, an Mts-1 encoding sequence is provided in an expression vector. Preferred expression vectors for use in a therapeutic composition include any appropriate gene therapy vectors, such as nonviral (e.g., plasmid vectors), retroviral, adenoviral, herpes simplex viral, adeno-associated viral, polio viruses and vaccinia vectors. Examples of retroviral vectors include, but are not limited to, Moloney murine leukemia virus (MoMuLV), Harvey murine sarcoma virus (HaMuSV), murine mammary tumor virus (MuMTV), and Rous Sarcoma Virus (RSV)-derived recombinant vectors. Gene therapy vectors can be made tissue specific by, for example, linking the Mts-1 encoding nucleotide sequence to a tissue-specific promoter. Multiple teachings of gene therapy are available to those skilled in the art, e.g., W. F. Anderson (1984) "Prospects for Human Gene Therapy" *Science* 226: 401–409; S. H. Hughes (1988) "Introduction" *Current Communications in Molecular Biology* 71: 1–12; N. Muzyczka and S. McLaughlin (1988) "Use of Adeno-associated Virus as a Mammalian Transduction Vector" Communications in *Molecular Biology* 70: 39–44; T. Friedman (1989) "Progress Toward Human Gene Therapy" *Science* 244: 1275–1281 and W. F. Anderson (1992) "Human Gene Therapy" *Science* 256: 608–613.

The nucleic acid molecule can be delivered "naked" by direct injection into the blood stream or to the desired tissue or organ of a subject. Alternatively, the nucleic acid molecule can be combined with a lipid compound which facilitates the uptake of the molecule by cells. The lipid compound include liposome, lipofectins, cytofectins, lipid-based positive ions, and then introduced into the body fluids, the blood stream, or a selected tissue site. Liposome mediated gene therapy is well known in the art and is described by, e.g., Lesoon-Wood et al., *Human Gene Ther.* 6: 395, 1995; Tsan et al., *Am. J. Physiol* 268: 11052, 1995; Vieweg et al., *Cancer Res.* 5585: 2366, 1995; Trivedi et al., *J. Neurochem.* 64: 2230, 1995; Hickman et al., *Human Gene Ther.* 5: 1477, 1994; Westbrook et al. *Human Mol Genet.* 3: 2005, 1994; Schmid et al., *Z. Gastroenterol* 32: 665, 1994; Hofland et al., *Biochem. Biophys. Res. Commun.* 207: 492, 1995; Plautz et al., *Ann. N.Y. Acad. Sci.* 7168: 144, 1994. Other DNA carriers which can facilitate the uptake of a desired vector by the target cells include nuclear protein, or ligands for certain cell receptors, which can be combined with a vector in engineered vesicles for delivery.

The angiogenic compositions of the present invention can include other substances that are appropriate or beneficial; for angiogenesis. These substances can include any other angiogenic compounds, growth hormones, growth factors, biologically active segments of growth factors, interleukins, polysaccharides, or mixtures thereof. Specific examples include, but are not limited to, pituitary growth hormones (hGH and bGH), various growth factors such as fibroblast growth factorsl(FGF), insulin-like growth factors (IGF), platelet-derived growth factors (PDGF), transforming growth factors (e.g., transforming growth factor alpha and beta), and other angiogenic compounds such as synthetic peptides Gly-His-Lys (GHK), Gly-Arg-Gly-Asp (GRGD) and Arg-Gly-Asp (RGD). See, e.g., U.S. Pat. Nos. 5,763,399 and 4,888,324, both of which are incorporated herein by reference.

Further in accordance with the present invention, the Mts-1 components are preferably provided in a pharmaceutically acceptable carrier. The carrier can be liquid, semisolid, e.g. pastes, or solid carriers. Except insofar as any conventional media, agent, diluent or carrier is detrimental to the recipient or to the therapeutic effectiveness of angiogenic substances contained therein, its use in practicing the methods of the present invention is appropriate. Examples of carriers include oils, water, saline solutions, gel, lipids, liposomes, resins, porous matrices, binders, fillers and the like, or combinations thereof.

Preferably, the carrier for use in the present methods is a controlled release matrix, a material which allows the slow release of angiogenic substances mixed or admixed therein. The release of angiogenic material can be slow or fast, depending upon the nature of treatment. Examples of such controlled release matrix material include, but are not limited to, sustained release biodegradable formulations described in U.S. Pat. No. 4,849,141 to Fujioka et al., U.S. Pat. No. 4,774,091 to Yamashira, U.S. Pat. No. 4,7103,108 to Silver et al., and Brem et al. (*J. Neurosurg.* 74: 441–446, 1991), all of which are incorporated herein by reference.

In accordance with the present invention, the Mts-1 components can be combined with the carrier in any convenient and practical manner, e.g., by admixture, solution, suspension, emulsification, encapsulation, absorption and the like, and can be made in formulations suitable for injections, implantations, inhalations, ingestions and the like.

In a further aspect of the invention, an angiogenic composition as described hereinabove is administered to a subject to enhance angiogenesis. Thus, the present invention provides methods of enhancing angiogenesis in a subject in need thereof by administering to the subject a therapeutically effective amount of an Mts-1 component, preferably, with a pharmaceutically acceptable carrier.

The angiogenic compositions of the present invention can be administered to the subject by standard routes, including the oral, ophthalmic nasal, topical, transdermal, parenteral (e.g., intravenous, intraperitoneal, intradermal, subcutaneous or intramuscular) intracranial, intracerebral, intraspinal, intravaginal, intrauterine, or rectal route. In addition, the angiogenicican be introduced into the body, by injection or by surgical implantation or attachment, proximate to a preselected tissue or organ site such that a significant amount of an angiogenic substance is able to enter the site, preferably, in a controlled release fashion, by direct diffusion to induce the vascularization into the site.

The dosage of an angiogenic Mts-1 component depends on the disease state or condition being treated and other clinical factors, such as weight and condition of the subject, the subject's response to the therapy, the type of formulations and the route of administration. The precise dosage to be therapeutically effective and non-detrimental can be determined by those skilled in the art. As a general rule, the therapeutically effective dosage of an Mts-1 protein or functional fragments thereof can be in the range of about 0.5 $\mu$g to about 2 grams per unit dosage form. A unit dosage form refers to physically discrete units suited as unitary dosages for mammalian treatment: each unit containing a pre determined quantity of the active material calculated to produce the desired theraputic effect in association with any required pharmaceutical carrier. The methods of the present invention contemplate single as well as multiple administrations, given either simultaneously or over an extended period of time.

All the publications mentioned in the present disclosure are incorporated herein by reference. The terms and expressions which have been employed in the present disclosure are used as terms of description and not of limitation, and there is no intention in the use of such terms and expressions of excluding any equivalents of the features shown and described or portions thereof, it being recognized that various modifications are possible within the scope of the invention.

EXAMPLE 1

MTS-1 Transgenic Mice Developed Hemangiomas and Stenosis

Pathologies of Transgenic Animals

Transgenic animals strains tg579, tg581, tg589 and tg595 bearing the S100A4(mts1) gene under control of an ubiquitous promoter of the housekeeping 3-hydroxy-3-methylglutarylCoA reductase gene were generated. Groups of transgenic animals and nontransgenic littermates were kept for up to 26 months in order to monitor any late appearances of abnormalities in their life. The amount of animals per group varies from 5 to 31. Animals with the signs of disease were sacrificed before the date. Animals were sacrificed and analyzed for existence of macroscopical abnormalities. Organs with abnormalities were fixed in 4% formaldehyde.

Pathological examination and immunostaining were carried out using anti-S100A4(mts1) and anti-smooth muscle action antibodies. Tissues were fixed in 4% formaldehyde in PBS. After paraffin embedding, 5 $\mu$M sections were prepared and stained with hematoxylin and cosin. Paraffin embedded sections were used for immunostaining with affinity purified anti-S100A4(mts1) rabbit polyclonal antibodies. Staining conditions were described as in Ambartsumian et al. (*Oncogene* 13:1621–1630, 1996). Rabbit anti-mouse IgG coupled with horse radish peroxidase (DAKO A7S, Denmark) and ImmunoPure metal enhanced DAB substrate (Pierce, USA) were used for visualization of positive cells. Monoclonal anti-$\alpha$-smooth muscle actin antibodies were used as a marker for detection of smooth muscle cells. Staining was performed according to the manufacturer's protocol (Sigma, USA). The antigen was visualized by incubation with FITS-conjugated anti-mouse fluorescent antibodies.

The animals of the HMGCR/mts1 transgenic strains were phenotypically normal and expressed enhanced levels of the S100A4(mts1) protein only in those organs that normally express the protein. No pathologies were associated with the young HMGCR/mts1 transgenes. A number of pathologies were observed for older animals after histopathological analysis. Lymphomas were detected in more than 10% of both transgenic and nontransgenic groups. Another two pathologies systematically detected only in transgenic animals were stenosis of lung arterias and hemangioma. See FIGS. 1,A and B. It is noted that Stenosis, an extreme development of smooth muscle cells surrounding the blood vessels has not been previously described in mice. Hemangiomas, which are benign tumors of vascular origin, are extremely rare in the populations of laboratory mice. The incidence of spontaneous hemangiomas in mice of different strains throughout their natural life span is 0.16–0.6% Peters et al.(*Int. J. Cancer,* 10:273–282, 1972), Frith et al. (*Lab. Anim. Sci.,* 32:157–162, 1982), Booth et al. (*Lab. Anim. Sci.,* 45:497–502, 1995). Among 17–26 month-old HMGCR/mts1 animals, the incidence of hemangiomas was more than 15%. Hemangiomas were detected in the skin, spleen, but mainly in the liver of transgenic animals. See Table 1.

TABLE 1

Incidence of pathologies in the HMGCR/mts1 transgenic mice

| Strain | Age/amount | Hemangioma | Stenosis | Lymphoma |
|---|---|---|---|---|
| | 02–16 months | | | |
| Tg595 | N = 4 | 0 | 0 | 0 |
| Tg579 | N = 15 | 0 | 0 | 0 |
| Tg581 | N = 9 | 0 | 10.5% | 5.2% |
| Tg589 | N = 10 | 10% | 0 | 10% |
| Control | N = 11 | 0 | 0 | 90% |
| | 17–24 months | | | |
| Tg595 | N = 5 | 40% | 0 | 0 |
| Tg579 | N = 31 | 9.6% | 6.4% | 9.6% |

TABLE 1-continued

Incidence of pathologies in the HMGCR/mts1 transgenic mice

| Strain | Age/amount | Hemangioma | Stenosis | Lymphoma |
|---|---|---|---|---|
| Tg581 | N = 23 | 17.4% | 4.5% | 17.3% |
| Tg589 | N = 19 | 10.5% | 5.2% | 15.7% |
| Control | N = 22 | 0 | 0 | 13.6% |

Both pathologies observed were connected to the hyperproliferation of the cells participating in the formation of blood vessels. Staining of the lungs with stenotic lesions with the antibodies to smooth muscle actin revealed that these lesions arose as a result of extreme development of the smooth muscle cells FIG. 1,C. Staining of these lungs with the antibodies to the S100A4(mts1) demonstrated that the hyperproliferated smooth muscle cells were not expressing the S100A4(mts1). In contrast, the cells surrounding the lesion (presumably pericytes) expressed the S100A4(mts1) FIG. 1,D. When the liver hemangiomas were stained with the S100A4(mts1) antibodies, the endothelial lining and smooth muscle cells were negative. However, increasing amounts of S100A4(mts1)-positive hepathocytes were detected in the area of hemangioma FIG. 1,E These observations indicate that expression of Mts-1 was down-regulated in young HMGCR/mts1 transgenic animals in a tissue-specific fashion. Late in life, a deregulation of such down-regulation took place that brought to the accumulation of the S100A4(mts1) in the organism, and as a consequence, to the development of pathologies. The fact that hyperproliferated cells themselves did not express S100A4(mts1), whereas the cells in the vicinity of the lesions were positive for the S100A4(mts1) expression, indicates that certain cells in the mouse organism secreted the Mts1 protein which accumulated and acted as a stimulator, stimulating the hyperproliferation of neighboring cells, particularly, endothelial cells.

Accumulation of S100A4(mts1)in the Blood of Transgenic Animals

To determine whether there was any Mts-1 protein accumulated in the blood stream of transgenic animals, immunoprecipitation experiments were carried out as follows. Serum was diluted 10 times in 1×RIPA and was subject to immunoprecipitation with anti-S100A4(mts1) rabbit serum, or normal rabbit serum as a negative control, followed by adsorption of the immuno-complexes on protein G Sepharose (Pharmacia, Sweeden). Samples were then separated by 15% SDS-polyacrylamide gel electrophoresis under reducing conditions, transferred by electroblotting onto Immobilon P membrane (Millipore, USA). Protein bands were visualized using the UCL system SuperSignal® (Pierce) according to the manufacturer's protocol. The results were illustrated in FIG. 2,A.

In order to quantitate the amount of the S100A4(mts1) protein in the blood stream, sandwich ELISA assays were performed as follows. None-Immuno Maxisorp 96 well plates (Life Technologies) were coated overnight at 4° C. with 4 µg of purified mouse anti-S100A4(mts1) monoclonal antibodies, HM4 (Kriajevska et al, 1994). Following incubation, the plates were blocked with 5% bovine serum albumin (BSA), 1 hour at room temperature. The mouse serum was added in dilution 1:20 (50 µl) in 5% BSA and incubated for 1 hour at room temperature. The secondary antibody, affinity purified rabbit anti-S100A4(mts1) in 1:75 dilution in 5% BSA, was added to the wells and the plates were incubated for 1 hour at room temperature. The complexes formed were visualized by sequential incubation with horse-radish peroxidase coupled goat anti-rabbit IgG (DAKO, A/S, Denmark) and chromogenic phenylenediamine dihydrochloride (OPD) substrate (DAKO, A/S, Denmark). The reaction was quantified on a standard ELISA reader. The ELISA was calibrated with recombinant S100A4 (mts1) in concentrations ranging from 0.2 to 20 ng/ml. The sensitivity was less than 2 ng/ml. All the incubations were accompanied by washes with PBS, 0.1% Tween-20.

FIG. 2,B depicts the results of measurements of the S100A4(mts1) protein in the blood serum of transgenic and nontransgenic animals. Nontransgenic animals contained some S100A4(mts1) in the blood stream in an amount higher than the background (FIG. 2, lanes 1 and 2). Transgenic animals of 2–16 months contained 1.24 ($p<0.037$) times more S100A4(mts1) protein in the blood serum compared to the nontransgenic ones. The amount of the S100A4 (mts1) in the blood stream of 17–26 months old transgenic animals was 1.73 times higher than the nontransgenic animals of same age (1.73 times, ($p>0.02$) (FIG. 2, lanes 3 and 4 respectively). The data clearly demonstrates the accumulation of the S100A4(mts1) protein in the blood serum of transgenic animals of old age.

EXAMPLE 2

S100A4(MTS1) Stimulates Neovascularization in an Mouse Cornea Assay

The mouse corneal assay was performed according to procedures previously described Jain, et al. (Nature Med. 3:1203–1208, 1997), Cao et al. (J. Exp. Med. 182:2069–2077, 1995) and Cao et al. (Proc. Natl. Acad Sci. USA 95:14389–14394, 1998). Corneal micropockets were created with a modified von Graefe cataract knife in both eyes of each male 5–6 wk-old C57B16/J mouse. A micropellet (0.35×0.35 mm) of sucrose aluminum sulfate (Bukh Meditec, Copenhagen, Denmark) coated with hydron polymer type NCC (IFN Sciences, New Brunswick, N.J.) containing 320 ng of MTS-1 was implanted into each pocket. The pellet was positioned 0.6–0.8 mm from the corneal limbus. After implantation, erythromycin/ophthalmic ointment was applied to each eye. The corneal neovascularization was examined by a slit-lamp biomicroscope on day 5 after pellet implantation. Vessel length and clock hours of circumferential neovascularization were measured. Ten corneas of five mice were used in each group.

The angiogenic response of corneas stimulated by S100A4(mts1) is illustrated in FIG. 3. The limbal vessels were dilated in the S100A4(mts1)—implanted corneas (B). The measured microvessel length (C), clock hours (D) and area (E) were significantly greater than the control corneas (C–E). Pellets containing sucrose aluminum sulfate alone did not induce corneal neovascularization (A). Thus, the S100A4(mts1) was able to induce an angiogenic response in mouse corneas.

EXAMPLE 3

S100A4(MTS1) Stimulates Motility of Endothelial Cells in vitro

The influence of the S100A4(mts1) protein on the endothelial cells was tested in vitro. Mouse endothelial SVEC4–10 cell line was obtained from the American Type Culture Collection (ATCC).

SVEC4–10 cultures were dislodged with a trypsin-EDTA solution (0.5 g/ml trypsin, 0.75 mM EDTA, Gibco BRI, Denmark) and seeded in six-well tissue culture plates (35 mm diameter wells) at a density of $3\times10^3$ cells/cm$^2$, and incubated for 24 h before video recording. Dishes were coated with Matrigel (10 µg/ml) (from a murine Enghelbertholm-Swearm tumor provided by Dr. Hynda K. Kleinman, National Institute of health, Bethesda, Md.D). In some cases cells were plated on bare plastic.

Time-lapse video-recording was done at intervals of 10 min for a period of 60 minutes using the software PRIMA (Protein laboratory, Copenhagen, Denmark), a black and white CCD video camera (Burle, Lancaster, Pa.) attached to the Nikon Diapot inverted microscope equipped with phase contrast optics, a computer movable stage which allowed simultaneous recording from several microscopic fields, and a plexiglas incubator (Nicon, Yokohama, Japan) with a thermostatically controlled heating fan (DFA, Copenhagen, Denmark) maintaining the temperature at 37° C.

Individual cell motility was determined as described by Walmod et al. (*Cell Motility and Cytoskeleton* 40:220–237, 1998) and Kustikova et al. (*Mol. And cell Biol.* 18:7095–7105, 1998). Briefly, the position of the center of the nucleus of individual cell in consecutive video frames was marked and cell tracks were subsequently generated using the image processing software. From the length of individual cell tracks the cell displacement, d, was determined and the mean cell speed at a time interval, $\tau$, of 10 min was calculated as $S_{10}=d/\tau$ Dunn G.A. (*Agents Action Supl.* 12:14–33, 1983). Data also were expressed as the mean-square-displacement of the cells ($d^2$) in relation to $\tau$, and fitted to the quation describing individual cell motility as a persistent random walk Walmod et al. (*Cell Motility and Cytoskeleton* 40:220–237, 1998).

$$\langle d^2 \rangle = 2S^2 P(\tau - P(1-c^{\tau/P})),$$

where S (distance/time) stands for the theoretical root-mean-square speed, P (time) stands for persistence time of direction. The rate of diffusion, R (distance $^2$/time) was calculated, R being equal to $2S^2P$.

Figure 4A:
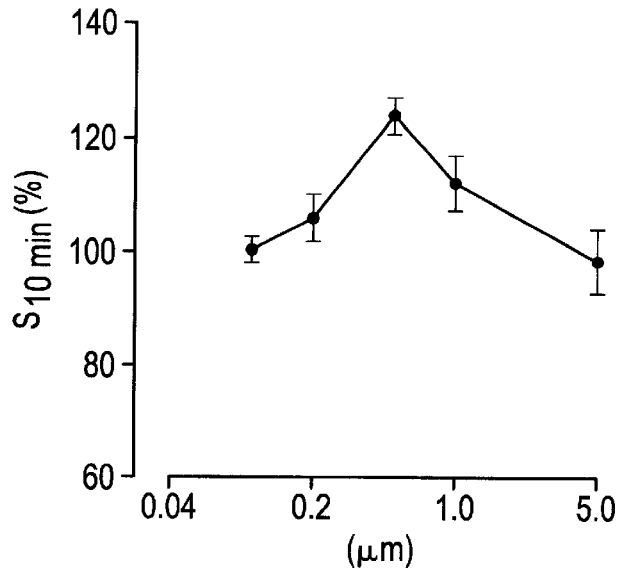
Figure 4B:
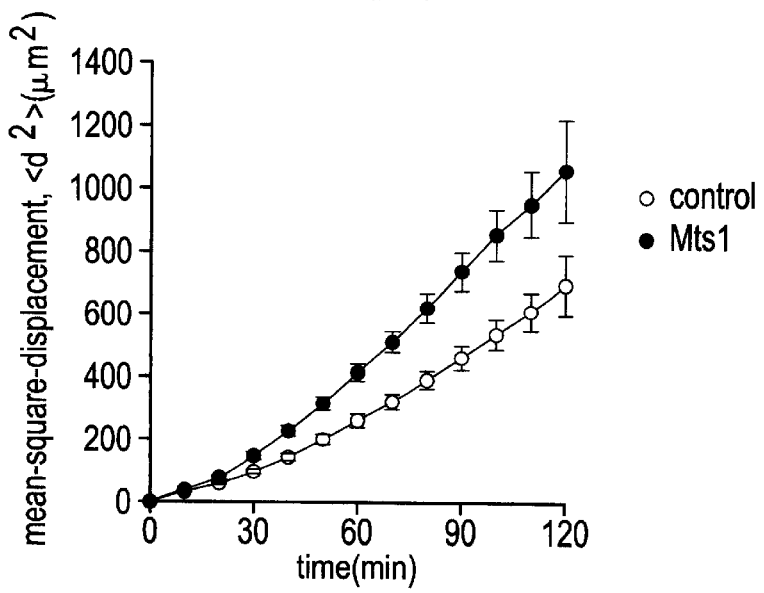

As shown in FIG. 4, recombinant S100A4(mts1) affected motility of SVEC4–10 cells in a dose-dependent manner. FIG. 4a shows that the mean-square speed of the cells increased by 24% at a concentration of 0.5 µM. In order to analyze the influence of the S100A4(mts1) on motile behavior of SVEC4–10 cells in more detail, the data were expressed as the mean-square-displacement of the cells ($d^2$), at time $\tau$ and fitted to the equation describing single cell motility FIG. 4b. Based on the curve fitting, the three major parameters were determined, which characterize cell motility of SVEC4–10 cells as a persistent random walk: the root-mean square speed (S), the time of persistence in direction (P) and the rate of diffusion (R).

Table 2 demonstrates that treatment of the cells with 0.5 µM S100A4(mts1) caused an increase of S and R and did not affect the persistence time, P. Increase in the rate of cell diffusion indicates that the scattering effect of S100A4 (mts1) occurred as a result of the increase in the cell speed rather than the time of persistence in direction.

Figure 4C:
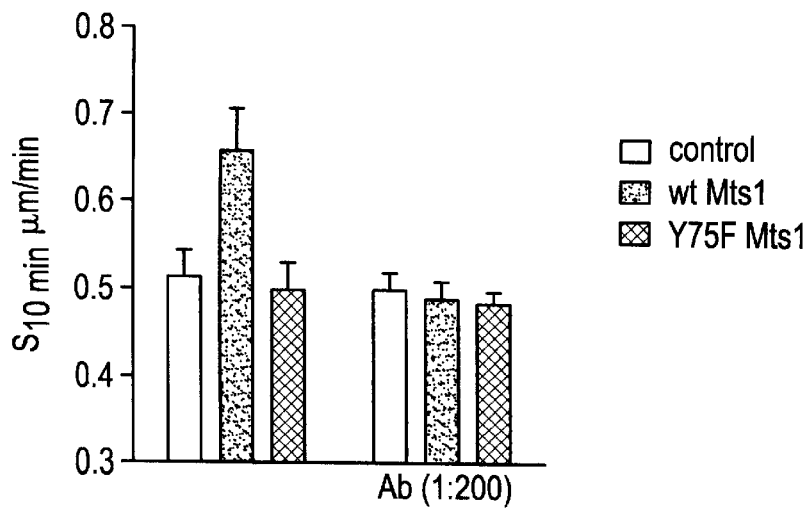

The specificity of the Mts1 effect on cell motility was demonstrated by addition to the media of the mutant form of the S100A4(mts1) Y75F. FIG. 4c indicates that the Y75F mutant of S100A4(mts1) had no effect on motility of SVEC4–10 cells. When the anti-S100A4(mts1) antibodies were added together with the S100A4(mts1) to the SVEC4–10 cells the stimulatory effect of the mts1 protein on the motility of the cells was diminished FIG. 4c.

Measurement of the proliferation rate of the SVEC4–10 in presence of the S100A4(mts1) by BrdU incorporation did not reveal any stimulatory effect of recombinant S100A4 (mts1) on proliferation of the SVEC4–10 cells.

TABLE 2

Root-mean-square-speed (S), rate of diffusion (R) and persistence time (P) of SVEC4-10 cells treated with recombinant S100A4 (mts1).

| Treatment | No of cells | S (µM/min) (mean ± SD) | R (µM²/min) (mean ± SD) | P (min) (mean ± SD) |
|---|---|---|---|---|
| Control | 75 | 0.36 ± 0.01 | 7.7±0.2 | 28 ± 2.5 |
| S100A4 (mts1) | 89 | 0.47 ± 0.01 | 11.2±0.22 | 25 ± 1.5 |

EXAMPLE 4

S100A4(MTS1) is Released by Tumor Cells and Stimulates Tumor Vascularization

To test the possibility of secretion of the S100A4(mts1) protein by tumor cells, two cell lines were analyzed: CSML100 cell line and VMRLiv cells transfected with the S100A4(mts1) under the control of a tetracycline-inducible promoter.

Mouse mammary adenocarcinoma cell line CSML-100 is highly metastatic and expresses high amounts of the S100A4 (mts1) protein Senin et;al. (*Vestnik USSR Acad. Med. Sci.* 5:85–91, 1984). VMR-liv is another mouse mammary adenocarcinoma cell line (Senin et al, 1984). These two cell lines were derived from two independent spontaneous tumors in A/Sn mice. Conventional tetracycline-inducible clones of VMR-Liv cells bearing the S100A4(mts1) gene were obtained according to the protocols as described by Gossen et al. (*Proc. Natl. Acad. Sci. USA* 89:5547–5551, 1992), and Gossen et al. *Science* 268:1766, 1995).

Cells were grown in Dulbecco Modified Eagle Medium (DMEM, Gibco BRL, Denmark), supplemented with 10(v/v) fetal calf serum (FCS), penicillin (100 U/ml) and streptomycin (100 µg/ml). Cells were incubated at 37° C. in a humidified atmosphere containing 5% $Co_2$.

Cells of VMR-Liv (tet-on) clone 137.188 were treated with 2 µg/ml doxycillin for 24 hours for S100A4(mts1) activation. After induction, cells were metabolically labeled for 2 h in methionine-cystein-free medium supplemented with dialyzed and inactivated 10% FCS with 0.2 mCi/ml [$^{35}$S]-methionine and -cystein (ICE, England). After labeling, the cells were washed, fresh conventional media was added, and the cells were incubated for different periods of time for monitoring the S100A4(mts1) release. The supernatants were collected and filtered through nitrocellulose filters 0.45µ (Millipore, USA).

1×RIPA buffer (150 mM NaCl, 1.0% NP-40, 0.5% DOC, 0.1% SDS, 50 mM Tris pH8.0) 1 mM DTT, 10 µg/ml leupeptin, 2 µg/ml aprotinin, 0.1 mM PMSF and 1 mM benzamidin were added prior the immunoprecipitation. Cells were lyzed in 1×RIPA buffer in the presence of protease inhibitors. Anti-S100A4(mts1) rabbit serum was used for immunoprecipitation followed by adsorption of the complexes on protein G Sepharose (Pharmacia, Sweeden). Normal rabbit serum was used as a negative control to the immunoprecipitation. Nonlabeled cell lysates and supernatants were prepared in the same way, except that conventional media was used.

Viability of the cells in these experiments was determined by measuring lactate dehydrogenase activity in the medium at each time point. The assay was performed according to the protocol of the manufacturer (Sigma, USA). Viability was found to be higher than 98% in all the experiments.

FIG. 5 demonstrates that, for both cell lines, S100A4 (mts1) was released into the culture media. $^{35}$S labeled S100A4(mts1) protein over expressed in the VMRLiv cells was secreted into the media and was immunoprecipitated by anti-S100A4(mts1) antibodies FIG. 5,A. S100A4(mts1) was also detected in the culture media of CSML100 cells. FIG. 5,B demonstrates the kinetics of the accumulation of the protein in the media. The protein immunoprecipitated from the media by anti-S100A4(mts1) antibodies was quantitated using Western blot analysis FIG. 5,B.

Next, the levels of vascularization of mammary tumors induced in the CRS.A nontransgenic mice and the GRS/A-mts1 hybrid transgenic mice over expressing S100A4(mts1) in the mammary gland were compared.

Sections of the tumors were stained for the mouse endothelial cell marker—CD31. Frozen sections of the tumors extracted from the GRS/A-mts1 hybrid and nontransgenic GRS/A tumor bearing females were used for immunohistochemical staining with rat monoclonal anti-CD31 (PECAM-1) antibodies (Pharm InGen, USA). Frozen tumor preparations were generated as described by Ambartsumian et al. (1996). Primary antibody was detected with alkaline phosphatase conjugated secondary rabbit anti-rat antibody (DAKO A/S, Denmark), followed by development with Fast Red System (Sigma, USA).

The blood vessel density was determined as described in Ferrara et al. (*Nature Medicine* 4:336–340, 1998). Sections were examined at x400 magnification with a 10×10 eyepiece grid (covering area 0.063mm$^2$). 20 random regions were selected in the tumor mass. Each square within the grid that contained positive endothelial cells was counted as a "hit". Thus, the maximal score was 100. All the slides were counted by blind method. Data shown are mean of determination of the vessel density of 10 tumors ±SD. Two-tailed students distribution was used for statistical analysis (P value<0.024).

FIG. 5,C demonstrates the mean values of the vessel density in 10 transgenic and 10 nontransgenic tumors. The mean vessel count in transgenic tumors expressing S100A4 (mts1) protein was 1.5 times higher than in nontransgenic ones (P<0.024).

We claim:

1. A method of enhancing angiogenesis in a tissue or organ of a subject in need thereof, which comprises administering an effective amount of a full-length Mts-1 protein to the subject at a site proximate to said tissue or organ.

2. The method of claim 1, wherein said tissue or organ is a damaged tissue or organ, or a transplant tissue or organ.

3. The method of claim 2, wherein said tissue is cardiac tissue, brain tissue, skin, tissue of gastrointestinal tract, or tissue of urinal tract.

4. The method of claim 2, wherein said organ is heart.

5. The method of claim 1, wherein said Mts-1 protein is provided in a pharmaceutical acceptable carrier.

6. The method of claim 5, wherein said carrier is oil, water, saline solution, gel, lipid, liposome, or a porous matrix material.

7. The method of claim 5, wherein said carrier is capable of a controlled release of said Mts-1 protein.

8. The method of claim 1, wherein said Mts-1 protein is administered to the subject via an oral, ophthalmic, nasal, topical, transdermal, parenteral, intracranial, intracerebral, intraspinal, intravaginal, intrauterine, or rectal route.

9. The method of claim 1, wherein said Mts-1 protein is administered to the subject by injection or surgical implantation proximate to a preselected tissue or organ site in need of angiogenesis.

* * * * *